United States Patent
Saito et al.

(10) Patent No.: US 7,129,492 B2
(45) Date of Patent: Oct. 31, 2006

(54) SYSTEMS AND METHODS FOR INSPECTING COATINGS

(75) Inventors: Kozo Saito, Lexington, KY (US); Mohammed I. Hassan Ali, Lexington, KY (US); Akira Numasato, Toyota (JP); Mohammed A. Omar, Lexington, KY (US); Masahito Sakakibara, Okazaki (JP); Toshikazu Suzuki, Aichi (JP); Yasuo Tanigawa, Hebron, KY (US)

(73) Assignees: Toyota Motor Manufacturing North America, Inc., Erlanger, KY (US); University of Kentucky Research Foundation, Lexington, KY (US)

( * ) Notice: Subject to any disclaimer, the term of this patent is extended or adjusted under 35 U.S.C. 154(b) by 273 days.

(21) Appl. No.: 10/629,426

(22) Filed: Jul. 29, 2003

(65) Prior Publication Data

US 2005/0023468 A1     Feb. 3, 2005

(51) Int. Cl.
G01N 21/88     (2006.01)

(52) U.S. Cl. .................................. 250/341.6

(58) Field of Classification Search .............. 250/341.6
See application file for complete search history.

(56) References Cited

U.S. PATENT DOCUMENTS

| | | | |
|---|---|---|---|
| 3,020,745 A | 2/1962 | Sielicki | |
| 4,633,594 A | 1/1987 | Bovone | |
| 4,634,291 A | 1/1987 | Bantel et al. | |
| 4,818,118 A * | 4/1989 | Bantel et al. | 374/7 |
| 4,996,426 A | 2/1991 | Cielo et al. | |
| 5,032,727 A * | 7/1991 | Cox et al. | 250/330 |
| 5,075,552 A | 12/1991 | McClelland et al. | |
| 5,111,048 A | 5/1992 | Devitt et al. | |
| 5,294,198 A | 3/1994 | Schlagheck | |
| 5,358,333 A | 10/1994 | Schmidt et al. | |
| 5,376,793 A | 12/1994 | Lesniak | |
| 5,711,603 A * | 1/1998 | Ringermacher et al. | 374/5 |
| 5,808,303 A | 9/1998 | Schlagheck et al. | |
| 6,000,844 A | 12/1999 | Cramer et al. | |
| 6,013,915 A * | 1/2000 | Watkins | 250/341.1 |
| 6,271,878 B1 | 8/2001 | Sera | |
| 6,339,337 B1 | 1/2002 | Matsuda et al. | |
| 6,346,704 B1 | 2/2002 | Kenway | |
| 6,399,949 B1 | 6/2002 | Roney, Jr. et al. | |
| 6,400,128 B1 | 6/2002 | Guidotti et al. | |
| 6,408,917 B1 | 6/2002 | Bett et al. | |
| 6,452,180 B1 | 9/2002 | Nistler et al. | |

(Continued)

FOREIGN PATENT DOCUMENTS

JP     62-198707     9/1987

(Continued)

OTHER PUBLICATIONS

N.P. Avdelidis, B.C. Hawtin and D.P. Almond "Transient Thermography in the Assessment of Defects of Aircrafts Composites" NDT and E International, vol. [36] Issue 6, pp. 433-439 Sep. 2003.

(Continued)

*Primary Examiner*—Albert Gagliardi
(74) *Attorney, Agent, or Firm*—Dinsmore & Shohl LLP

(57) ABSTRACT

A system for detecting defects in paint coatings includes a temperature manipulation apparatus configured to change the temperature of a surface and a coating applied to the surface. The system may further include an infrared sensor for measuring the change in temperature of the surface and coating and a processor to compare the measured change in temperature of the surface and coating to an expected change of temperature in order to determine anomalies in the coatings.

5 Claims, 5 Drawing Sheets

U.S. PATENT DOCUMENTS

| | | | |
|---|---|---|---|
| 6,461,035 | B1 | 10/2002 | Meinlschmidt et al. |
| 6,491,426 | B1 | 12/2002 | Schonath et al. |
| 6,515,284 | B1 | 2/2003 | Walle et al. |
| 6,517,238 | B1 | 2/2003 | Sun et al. |
| 6,751,342 | B1* | 6/2004 | Shepard ..................... 382/141 |
| 2002/0018510 | A1* | 2/2002 | Murphy et al. ............... 374/45 |
| 2002/0050566 | A1* | 5/2002 | Nilsson et al. ........... 250/341.6 |

FOREIGN PATENT DOCUMENTS

| | | |
|---|---|---|
| JP | 63-085438 | 4/1988 |
| JP | 1156650 | 6/1989 |
| JP | 02-022547 | 1/1990 |
| JP | 6341965 | 12/1994 |
| JP | 08-145922 | 6/1996 |
| JP | 10-096705 | 4/1998 |

OTHER PUBLICATIONS

E. Grinzato, V. Vavilov, T. Kauppinen. "Quantative Infrared Thermography in Buidings" Energy and Buildings 29, pp. 1-9 1998.

Ch. Maierhofer, A. Brink, M. Röllig and H. Wiggenhauser "Detection of Shallow Voids in Concrete Structures with Impulse Thermography and Radar" NDT and E International, vol. [36] Issue 4, pp. 257-263, Jun. 2003.

P.J. Fito, M.D. Ortolá, R.D. De los Reyes, P. Fito and E. De los Reyes "Control of Citrus Surface Drying by Image Analysis of Infrared Thermography" Journal of Food Engineering, vol. [61] Issue 3, pp. 287-290, Feb. 2004.

Balageas D. Deom A. Boscher D., "Characterization and Nondestructive Testing of Carbon-epoxy Composites by a Pulsed Photothermal Method." Materials Evaluation, vol. 45, 1987.

D.P. Almond and S.K. Lau "Defect Sizing by Transient Thermography. I: An Analytical Treatment" *J Phys D: Appl Phys* vol. [27] pp. 1063-1069, 1994.

M.B. Saintey and D.P. Almond "Defect Sizing by Transient Thermography. II: A Numerical Treatment" *J Phys D: Appl Phys* vol. [28] , pp. 2539-2546, 1995.

N.K. Del Grande and P.F. Dubrin, "Mapping Hidden Aircraft Defect with Dual Band Infrared Computed Tomography" Proc. Of SPIE V. 2455 Jun. 6-8, 1992, pp. 82-93.

N.P. Avdelidis and D.P. Almond "Transient Thermography as a Through Skin Imaging Technique for Aircraft assembly: Modeling and Experimental results" Infrared Physics and Technology, vol. [45] Issue 2, pp. 103-114, Mar. 2004.

H.G. Walther "Surface Roughness Influence on Photothermal Radiometry" Applied Surface Science, vol. [193] Issue 1-4, pp. 156-166, Jun. 2002.

S. Shepard, B.A. Rubadeux and t. Ahmed "Automated Thermographic Defect Recognition and Measurement." Nondestructive Characterization of Materials 1X, American Institute of Physics 1999.

Takahide Sakagami, Shiro Kubo "Applications of Pulse Heating Thermography and Lock-in Thermography to Quantative Nondestructive Evaluations" Infrared Physics and Technology vol. [43] pp. 211-218 2002.

Gary Shubinsky "Visual & Infrared Imaging for Bridge Inspection" Northwestern University BIRL Basic Industrial Research Laboratory, Jun. 1994.

Osiander R. Spicer JWM, Murphy JC. "Analysis Methods for Full-Field Time Resolved Infrared Radiometry" in Burleigh DD, Spicer JWM ed, Thermosense XVIII SPIE, Proc. 2766 pp. 218-227, 1996.

L.D. Favro, Xiaoyan Han, and R.L. Thomas "Thermal-Wave Imaging for NDE of Composites" pp. 1077-1081, Proceedings of the American Society for composites Twelfth Technical Conference: Oct. 6-8, 1998, Dearborn Inn, Dearborn Michigan D.J. Titman Applications of Thermography in Non-destructive Testing of Structures: NDT and E International vol. [34] pp. 149-154, 2001.

A. Wyckhuyse, X. Maldague, "Study of Wood Inspection by Infrared Thermography, Part I: Wood Pole Inspection by Infrared Thermography" Research in Nondestructive Evaluation, 13. Issue 1, pp. 1-12, Mar. 2001.

A. Wyckhuyse, X. Maldague, "Study of Wood Inspection by Infrared Thermography, Part I: Wood Pole Inspection by Infrared Thermography" Research in Nondestructive Evaluation, 13. Issue 1, Mar. 2001.

V. Vavilov, V. Demin, "Infrared Thermographic Inspection of Operating Smokestacks" Infrared Physics and Technology 43. pp. 229-232, 2002.

S. Shepard, R. Ducar. "Quantative Infrared Defect Detection in composite Aerospace Structures." 45th International SAMPE Symposium 2000.

T. Sakagami, S. Kubo, K. Sekine. "Development of a thermographic NDTtechnique for detection of latent blister in corrosion protective coating on oil storage tank", Thermosense XXIII Proc, 4360, Orlando, Florida 2001.

P.G. Bison, S. Marinetti, E. Grinzato, V. Vavilov, F. Cernuschi, Dr. Robba "Inspecting thermal barrier coatings by IR thermography" Thermosis XXV, K. Elliot Cramer, Xavier P. Maldague, Editors, Proceedings of SPIE 5073 (2003).

Oslander R, Spicer JWM, Murphy JC, "Analysis methods for full field time resolved radiometry" in Burleigh DD, Spicer JWM, eds. Thermosense XVIII, SPIE Proc. 2766:218-227, 1996.

Turler D. "Predicting the geometry and location of defects in adhesive and spot welded lap joints using steady state thermographic techniques" Thermosense XXI, 3700 Orlando-Florida, pp. 54-62, Apr. 6-8, 1999.

H. Aglan, S. Shroff, Z. Abdo, T. Ahmed, L. Wang, L.D. Favro and R.L. Thomas. "Cumulative fatigue disbond of adhesive joints and its detection using thermal wave imaging" Review of progress in quantitative non-destructive evaluation. 14, p. 431-438, 1995.

D.A. Tossell "Numerical analysis of heat input effects in thermography" Journal of nondestructive testing 6 No. 2 1987.

X. Maldague, F. Galmiche, A. Ziadi "Advances in pulsed phased thermography". Infrared Physics and Technology 43, pp. 175-181, 2002.

S. Shepard, J. Lahota, B. Rubadeux, T. Ahmed "Reconstruction and enhancements of active thermographic images sequence" Optical Engineering 42 (5) pp. 1337-1342, May 2003.

X. Maldague, J. Cote, D. Poussart, V. Valvilov "Thermal Tomography for NDT of industrial materials" Canadian Society of Nondestructive Testing Journal pp. 22-32, May-Jun. 1992.

Vavilov V. "Dynamic Thermal Tomography: Perspective Field of Thermal NDT" in Semanovich SA, ed. Thermosense XI, SPIE Proceedings, 1313. pp. 178-182, 1990.

V. Vavilov, X. Maldague "Dynamic Thermal Tomography: New Promise in the IR Thermography of Solids" SPIE vol. 1682, Thermosense XIV, pp. 194-206.

Feeler, Robert A., "Infrared Thermography Offers New Possibilities for Nondestructive Testing," Flight Safety Foundation, Aviation Mechanics Bulletin, May-Jun. 1995.

"Heat Conduction in Solids with Buried Discontinuities," Nondestructive Testing Handbook, Infrared and Thermal Testing, Third Edition, vol. 3, p. 62.

Favro, L.D., Xiaoyan Han, P.K. Kuo and R.L. Thomas, "Measuring Defect Depths by Thermal-Wave Imaging,"Thermosense XVIII: An International Conference on Thermal Sensing and Imaging Diagnostic Applications, vol. 2766, pp. 236-239, Mar. 1996.

L.D. Favro, et al. "*Thermal Wave Imaging of Aircraft Structures*" Review of Progress in Quantitative Non-destructive Evaluation, vol. 14, pp. 461-466, ©1995, Plenum Press.

Xavier P. V. Maldague, *Theory and Practice of Infrared Technology for Nondestructive Testing*, John Wiley & Sons, Inc. © 2001; Title page; copyright page; pp. 1-11; pp. 453-537; first two paragraphs of Section 7.4.3; pp. 204-235.

* cited by examiner

SYSTEMS AND METHODS FOR INSPECTING COATINGS

FIELD OF THE INVENTION

This invention relates to systems and methods for detecting defects in coatings applied to substrates. More particularly, this invention relates to systems and methods for detecting surface and subsurface defects in vehicle paint coatings using an infrared camera.

BACKGROUND OF THE INVENTION

One of the most important methods in high quality automobile and other vehicle or machine production involves the inspection of the exterior appearance (i.e. the quality of the paint finish). Usually, an automobile shell, for example, receives at least four coatings including a protective coat, an adhesion aid coat, a paint coat and a clear coat. Defects occurring in the coating method of a properly prepared surface that may diminish the perceived quality of the exterior paint include, but are not limited to, dust, hair, metallic particles, over spray, incomplete spray, stripping and flake penetration. Inspection for such defects will insure the exterior quality of the product from the customer's point of view.

Previously, evaluation of the quality of the paint finish was often based on human inspection, which can be a tedious and subjective method and one that requires meaningful skill and training. Other inspection procedures have been based on the use of charge-coupled device (CCD) optical sensors that sense imperfections through light reflected off of the finished surface. However, this technique is not particularly effective for complex, curved and/or hidden geometries (i.e. automobile bodies) because of its sensitivity and dependence on reflection and scattering angles.

In addition, it has been generally known to use infrared cameras to inspect certain products (i.e. semiconductor chips) for surface anomalies or defects. However, such inspection techniques are based solely on the spatial analysis of pixel values with that of known (standard) values without any account for the temporal behavior of the pixel values. Stated differently, because these techniques only view a surface and compare a captured view with a known signature, without consideration of the change of temperature over time, these techniques are generally only practical for use to inspect surface, as opposed to subsurface, anomalies.

As such, there is a desire for systems and methods capable of inspecting not only surface, but subsurface anomalies in multi-layered paint coatings.

SUMMARY OF THE INVENTION

Accordingly, the present invention is intended to address and obviate problems and shortcomings and otherwise improve previous systems and methods for inspecting coatings on surfaces, and particularly for automotive paints and coatings.

To achieve the foregoing and other objects and in accordance with the exemplary embodiments of the present invention, a system for detecting defects in coatings comprises a temperature manipulation apparatus configured to change the temperature of the surface and the coating, an infrared sensor configured to measure the change in temperature of the surface and the coating and a processor configured to compare the measured change in temperature of the surface and the coating to an expected change of temperature.

To still further achieve the foregoing and other objects of the present invention, a system and method for detecting defects in coatings comprises the steps of measuring a thermal profile of a surface to create a thermal signature, applying a first coating to the surface, changing the temperature of the coated surface, taking a first measurement of emitted radiation from the coated surface and comparing the emitted radiation to the thermal signature. The method also comprises the steps of applying a second coating to the coated surface, changing the temperature of the coated surface, taking a second measurement of emitted radiation from the coated surface and comparing the first measurement to the second measurement.

To yet further achieve the foregoing and other objects in accordance with other exemplary embodiments of the present invention, a system and method for detecting defects in coatings comprises the steps of applying a plurality of coatings to a surface, configuring an expected change of temperature, manipulating the temperature of the coated surface, measuring the change of temperature in the normally manipulated coated surface and comparing the measured change of temperature in the manipulated surface to the expected change of temperature.

To even further achieve the foregoing and other objects in accordance with additional exemplary embodiments of the present invention, a system and method for detecting defects in coatings comprises the steps of measuring a thermal profile of a surface to create a thermal signature, applying a first coating to the surface, and changing the temperature of the coated surface. The method further includes the steps of taking a first measurement of amount of emitted radiation from the coated surface, comparing the emitted radiation to the thermal signature, applying a second coating to the first coating, changing the temperature of the coated surface, taking a second measurement of amount of emitted radiation from this coated surface and measuring change in temperature thereof. The method also includes the steps of configuring an expected change of temperature, comparing the first measurement to the second measurement and comparing the measured change in temperature of the coated surface to the expected change of temperature.

Still other embodiments, combinations, advantages and objects of the present invention will become apparent to those skilled in the art from the following descriptions wherein there are shown and described alternative exemplary embodiments of this invention for illustration purposes. As will be realized, the invention is capable of other different aspects, objects and embodiments all without departing from the scope of the invention. Accordingly, the drawings, objects, and description should be regarded as illustrative and exemplary in nature only and not as restrictive.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF EXEMPLARY EMBODIMENTS

The principle of defect detection in the present invention is that when the temperature of a surface and/or coating(s) bearing such defects is manipulated and viewed by an infrared sensor, the defects will be effectively magnified and distinguishable as spots of different thermal imprint or color. More particularly, the thermal characteristics or effusivity difference between the defect and the surrounding paint or surface creates a thermal mismatch. The thermal mismatch results in a different thermal wave reflection from the defect as compared with its surroundings. The concept of thermal mismatch may be represented by the formula:

$$\Gamma = \frac{\sqrt{k_1 p_1 c_1} - \sqrt{k_0 p_0 c_0}}{\sqrt{k_1 p_1 c_1} + \sqrt{k_0 p_0 c_0}}$$

wherein k=thermal conductivity, p=density and c=specific heat. Sub 1 indicates properties of the defect whereas sub 0 indicates properties of the surroundings.

Because effusivity $e = \sqrt{k \cdot p \cdot c}$, then:

$$\Gamma = \frac{e_1 - e_o}{e_1 + e_o}$$

Accordingly, thermal mismatch is the difference between the thermal properties or characteristics (effusivity) of the defect and its surroundings as sensed by the sensing mechanism (e.g., the infrared camera or sensor, as will be discussed further below). For example, in determining the thermal mismatch between an air pocket and resin epoxy, wherein the air pocket (defect) has a known thermal effusivity of 9.19 W. $(sec.m^{-2}.K^{-1})^{0.5}$ and the epoxy resin (surroundings) has a known thermal effusivity of 667 W. $(sec.m^{-2}.K^{-1})^{0.5}$ $$\Gamma \text{ (thermal mismatch)} = \frac{e_1 - e_o}{e_1 + e_o} = \frac{9.19 - 667}{9.19 + 667} \approx -0.97$$

Accordingly, in this example, only approximately 97% of the thermal wave will reflect from the air pocket interface as compared with the epoxy resin, thereby causing a deviation in the temperature profile between the air pocket and the epoxy resin at that particular spot.

As a result of the thermal mismatch between the defect and its surroundings, thermal contrast profiles, which account for the speed of the change in temperature of the defect as compared to the speed of change of its surroundings, can be established. More particularly, because the different effusivity values of the defects result in a different rate of cooling ΔT compared with its surroundings, the contrast between the defect and its surroundings can be observed The concept of thermal contrast ($T_c$) may be represented by the formula:

$$T_c = \frac{T_d(t) - T_d(t_o)}{T_s(t) - T_s(t_o)}$$

wherein T=temperature, t=temperature, d=defective spot and s=non-defective spot. Accordingly, thermal contrast is the deviation in the measured temperature profile ΔT and the normal (expected) profile due to the existence of a foreign material or excess or absence of coating material(s) (e.g., defect).

Figure 1:
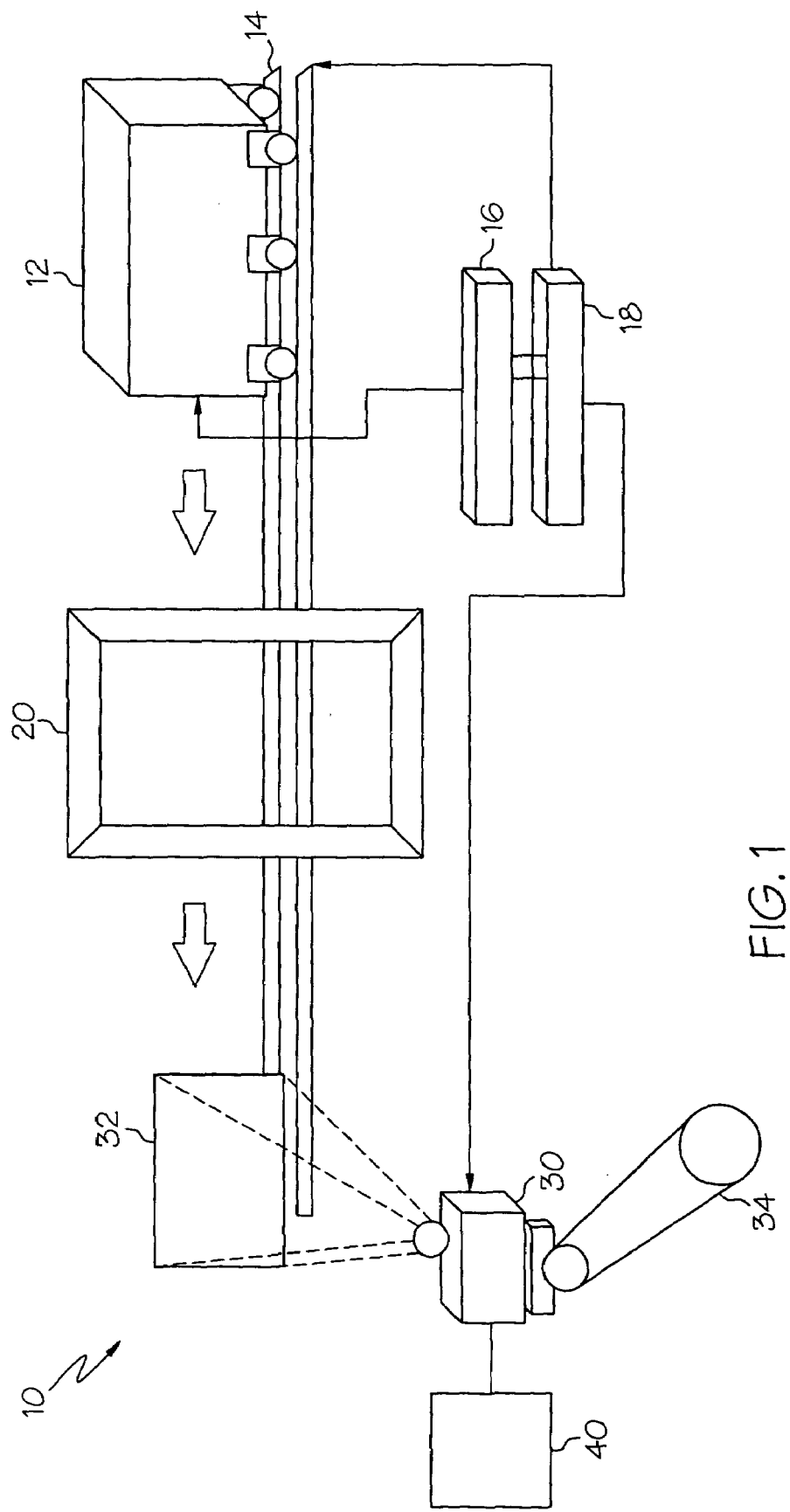
FIG. 1 is a schematic view of an exemplary system and method for creating a thermal signature in accordance with the present invention.

Applying these principles, the systems and methods of the present invention, in one or more of the embodiments, are capable of detecting defects in single and multi-layered coatings by measuring emitted radiation and comparing that measurement to a known thermal signature or a previously measured thermal profile. Referring to the drawing figures in detail, wherein like numerals indicate the same elements throughout the drawing figures, FIG. 1 illustrates at least part of an exemplary system 10 for viewing and determining a thermal profile. The exemplary system of FIG. 1 may be applied to a situation where a surface, herein referred to as a shell or workpiece 12, is raw (e.g. does not have a coating) and a thermal profile of the shell may be measured to create a thermal signature for later comparison to the thermal profile of same shell with one or more coatings (described later herein). Of course, shell 12 could comprise a complete vehicle body, portions of a vehicle, or a single piece to be coated. Alternatively, the exemplary system of FIG. 1 may also be applied to a situation wherein shell 12 comprises one or more coatings and the thermal profile of the shell and coatings is sought to be measured to check for defects. For purposes of this example, however, it is assumed that shell 12 is raw and/or that the coatings of interest have yet to be applied.

As illustrated in FIG. 1, the exemplary system 10 may comprise a temperature manipulation apparatus 20, a sensing mechanism such as an infrared (IR) sensor 30, and a processor 40. In this example, temperature manipulation apparatus 20 is illustrated as comprising a curing oven. Curing ovens are often used in the industry to "bake" a coating or layer of paint to the surface of an automobile shell. In the present invention, not only does the curing oven function to "bake" coatings and/or paint onto the shell 12, but also provides appropriate temperature manipulation of the shell and coatings so that emitted radiation and change of temperature may be optimally measured by IR sensor 30 (discussed later herein). As known in the industry, such a curing station or oven can comprise a plurality of heater banks and/or other elements to raise the temperature of the shell, its surfaces to be coated and/or the coating(s) applied as appropriate. In an exemplary embodiment for applying paint and/or other surface coatings to automobile panels or the like, the temperature of the curing oven may be set in the range of 150–250° C. This range has been found to be particularly effective to ensure proper "baking" of a coating while manipulating the temperature of the shell (and coatings) so that a desired thermal profile can be measured.

In another embodiment, however, curing oven 20 may be set at any desired temperature to adequately "bake" or cure a coating and/or provide optimal conditions to measure a thermal profile. In addition, it should be understood that because the present invention is directed toward detecting defects through measurements of emitted radiation and change of temperature during any heat transition, the temperature manipulation apparatus may also include any combination of heating and/or cooling devices used to manipulate the temperature test surface (and coatings) to provide optimal measurement of a thermal profile. In this regard, it should be understood that the "manipulation" contemplated can comprise increasing or decreasing relative temperatures. Such combinations include, but are not limited to application of a coating at a different temperature than the shell surface to create a measurable temperature differentiation therebetween and/or measuring the thermal profile of the shell 12 while the subject surface is being heated. Such combinations may further include use of sound waves or ultrasound waves that are converted to thermal energy inside the material and then detected by the IR sensor or other appropriate sensing mechanism.

Once the temperature of the shell 12 is manipulated in the curing oven 20, shell 12 may be inspected by IR sensor 30. As illustrated in FIG. 1, IR sensor 30 may be configured with a predetermined field of view 32 for inspecting shell 12. IR sensor 30 may be appropriately positioned to inspect shell 12 as the result of input from shell recognition sensor 16 and belt speed sensor 18. For example, shell recognition sensor 16 may be integrated, or configured to communicate with the IR sensor 30 and/or processor 40 for determining the type of shell or workpiece entering the curing oven 20. The recognition of the shell may be useful to assure that the IR Sensor 30 is calibrated and situated to capture an appropriate field of view 32 (e.g. size or angle) for the specific shell 12. In addition, belt speed sensor 18 may be integrated with the IR Sensor 30 and/or processor 40 for determining the speed of the belt 14 so that the IR Sensor may be synchronized or matched to position itself at a starting position appropriately and move around shell 12 on robotic arm 34. Also, IR sensor may be stationary and situated to take snap shots (e.g., plan or side views). In another embodiment, any combination of sensors and/or logic may be integrated with IR sensor 30 so as to properly position one or more IR sensor 30 to measure the desired field of view 32.

Still referring to FIG. 1, a delay between the time that shell 12 exits the curing oven 20 and is measured by the IR sensor 30 may be desired for multiple reasons. For example, it is believed that at the time when shell 12 first exits curing oven 20, shell 12 may still be absorbing heat, and therefore, may provide a varying emission of radiation for measuring the thermal profile. Accordingly, it is believed that it may be desirable to take measurements at some point during the cooling (i.e., after maximum temperature achieved) of the shell and/or coating(s) depending on the shell type and composition, and any associated coatings. As previously discussed, however, the present invention contemplates the use of any combination of heating and cooling to provide a temperature at which optimal radiation is emitted for measurement.

In addition, a delay between the curing oven 20 and measurement by the IR sensor may be desired in accordance with a calculated maximum contrast for the shell 12. More particularly, it is believed that as a result of the different thermal properties among various shells and/or layered coatings bearing defects, an optimal time window will generally exist for viewing a maximum thermal contrast (e.g. deviation in the measured temperature profile $\Delta T$ and the normal or expected profile due to the existence of a foreign material). For example, when a workpiece or shell has cooled to near room temperature, less thermal contrast will generally be detectible, and as a result sensitivity or accuracy of the defect detection will be reduced. As discussed later herein, by measuring the shell 12 during its particular window of thermal maximum contrast, focus may be given to the depth of a potential defect in one or more layers of a multi-layered coating.

IR sensor 30 may comprise any sensor or sensing arrangement configured to at least measure radiation emitted from a surface and/or the change of temperature of a surface over a period of time. For example, IR sensor 30 of the above example may be a TVS 8500 manufactured by CMC Electronics which is capable of achieving excellent observation ranges for the present invention of about 3 to 5 µm (Wavelength) at a temperature range of <40° C. over ambient temperature. While such observation ranges are currently believed to be particularly applicable for automotive coatings which have relatively low curing temperatures of about 200° C. or less, other observation ranges are contemplated by the present invention.

IR sensor 30 may change the field of view 32 through manual and/or automatic focusing of its lenses or by positioning itself at a proper location relative to shell 12 such as through appropriate positioning of robotic arm 34. Accordingly, while it is contemplated that only one IR sensor 30 might be needed to capture all desired fields of view 32, it should be understood that any number of IR sensors may be used to together to capture any number of fields of view. In such embodiment, IR sensors may be temporarily synchronized to compare temperature contrasts at same time.

As illustrated in FIG. 1, IR sensor 30 can measure an initial or base emitted radiation (a thermal profile) from the raw shell 12 by establishing an appropriate field of view 32. As discussed later herein, IR sensor 30 may map an area under a field of view into a grid, wherein each square or pixel of the grid may reflect a desired area to measure. If the raw shell is acceptable (e.g. does not comprise fatal defects such as cracks, dents, etc. that may prevent subsequent acceptable coating), a thermal signature for the shell may be created.

The thermal signature of the shell 12 may be stored in processor 40 or elsewhere for access by processor 40. Processor 40 may include, for example, any memory or computer configured to log data and perform comparison and analysis of data recorded. The thermal signature may be used as a template to be later compared with the thermal profile of the shell with one or more coatings for detection of defects. More particularly, because the thermal signature may provide a template (i.e. a map of any preexisting acceptable flaws or defects), defects detected upon comparison to a thermal profile taken of the shell 12 with one or more coatings can be distinguished from the flaws/defects already known to be existing on the shell.

Another unique feature of this system and method is that multiple thermal signatures for a variety of shells may be created and stored within processor 40 (or so that processor 40 has access to them). For example, recognition sensor 16 may sense the geometries of the shell and transmit signals regarding the geometries to processor 40 to discover whether an applicable thermal signature or one for a similar model has been created. If so, shell may be diverted directly to Paint Station I 60, described below. Alternatively, if processor 40 does not recognize shell 12, shell 12 may be directed through system 10 to create a thermal signature. In another embodiment, shell 12 may include an identification tag or other identifying apparatus configured to transmit signals to the IR sensor or processor regarding shell type. Because the system of the invention is capable of establishing a distinct thermal signature for each shell, different shell models may follow each other along beltline 14.

Figure 2:
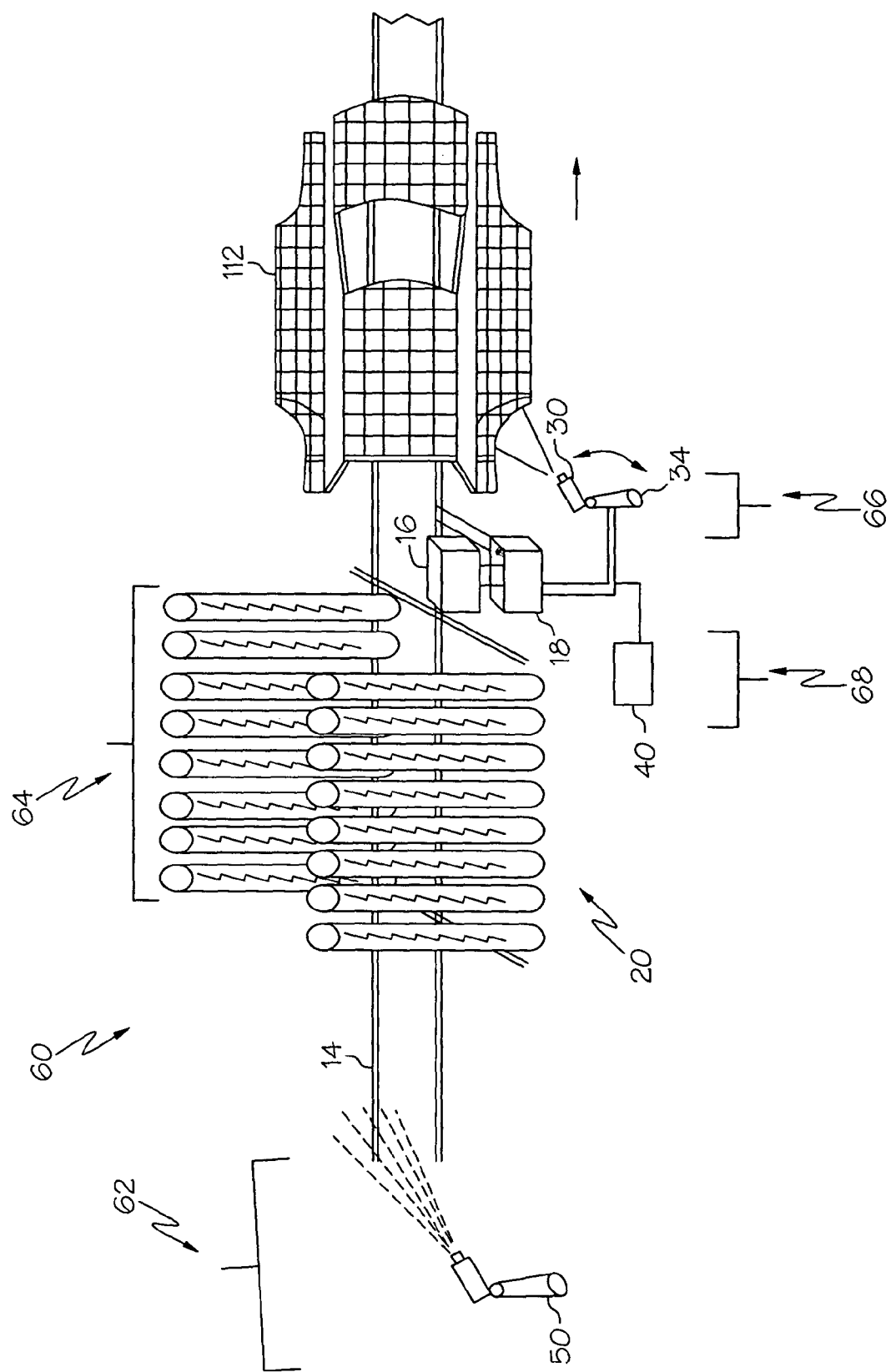
FIG. 2 is a schematic view of an exemplary station in a system and method for coating a surface and measuring a thermal profile in accordance with the present invention.

Once a thermal signature has been created and stored for a particular shell 12, the shell may be moved to a first coating station. Referring to FIG. 2, a first coating station is illustrated as Paint Station 1 60. For purposes of this example, the exemplary system illustrated in FIG. 2 comprises similar components as that of FIG. 1 with the addition of application apparatus 50. As later discussed herein, an exemplary coating station, such as Paint Station I, may be configured to measure not only the thermal profile of shell 12 with one or more coatings, but also the change in temperature of shell 12 and any associated coatings after temperature manipulation.

Paint Station I 60 is illustrated as comprising a coating application apparatus 50, a temperature manipulation apparatus 20, an infrared sensor 30 and a processor 40. As illustrated in FIG. 2, application apparatus 50 may comprise a paint gun or electrostatic spraying device as generally known in the industry configured to apply paint or another desired coating to a surface such as automobile shells. In another embodiment, any apparatus configured to apply paint and/or any other coating to a surface may be used.

Similar to FIG. 1, temperature manipulation apparatus 20 may comprise a curing oven configured to heat the shell and first coating 112 from application apparatus 50. As previously discussed, temperature manipulation apparatus 20 may also comprise any combination of heating and/or cooling elements or apparatuses configured to manipulate the temperature of the shell and/or coating 112. Such elements might include heat lamps, infrared heating elements, convection areas, microwave heaters or the like. As illustrated in FIG. 2, car recognition 16 and belt speed 18 sensors may be positioned on the opposite end of curing oven 20 to sense the shell 112 and belt speed once the shell 112 has exited the curing oven 12. As also to be understood, bar code renders, optical sensors, contact switches or other identification equipment and/or alignment arrangements can also be utilized to properly queue a shell 112 for IR sensing. As discussed above, such sensors may be used to appropriately position IR sensor 30 to capture an appropriate field of view.

The systems described above and illustrated in FIGS. 1 and 2 can be used, for example, to inspect automobile shells only and automobile shells with coatings applied thereto for defects that may deteriorate the exterior appearance of the automobile. Moreover, the present invention contemplates multiple methods of inspecting automobile coatings utilizing the systems set forth above. For example, one method of inspecting a multi-layered coating for defects includes analysis of each successive layer of coating with comparison to a previous layer. More specifically, the thermal profile for a coating may be compared with the thermal profile measured from a previous coating to determine the existence of a new or unresolved defect. Accordingly, a number of coating and inspection stations, similar to Paint Station I, may be linked together to create a complete coating line wherein each of the coating stations is configured to communicate data regarding previous coating stations, as well as statistical method data throughout the coating line.

Figure 3:
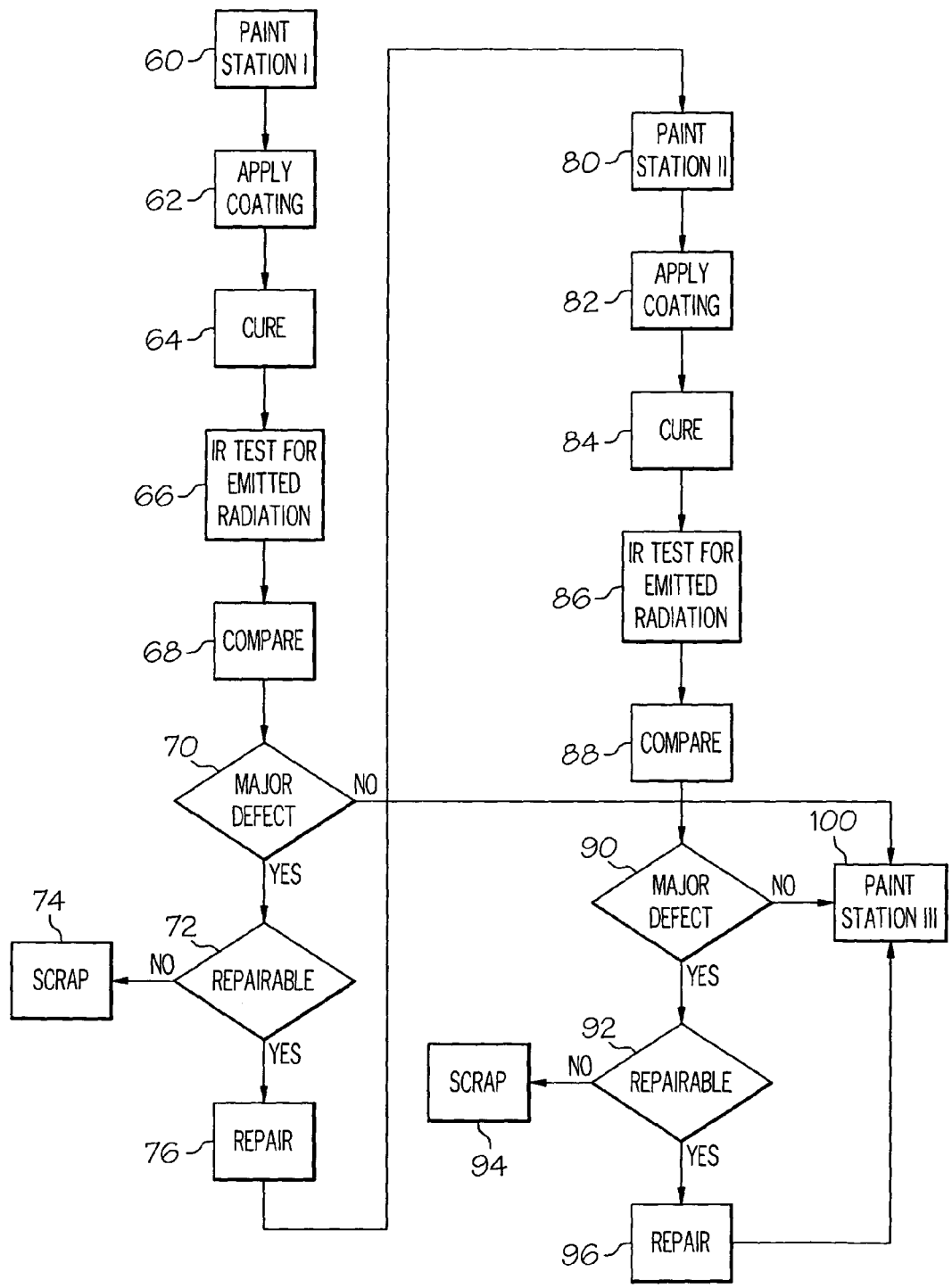
FIG. 3 is a simplified flow chart illustrating exemplary steps in a method of inspecting coatings in accordance with the present invention.

Referring the FIG. 3, exemplary steps for a method for inspecting a multi-layered coating for defects is illustrated. For purposes of this example, it is assumed that a thermal signature for the raw shell (e.g. 12 in FIG. 1) has been created or is otherwise known. Referring to FIGS. 1–3, raw shell 12 progresses to Paint Station I 60 for coating. Once the coating is applied 62, the shell (112 in FIG. 2) may be moved to temperature manipulation apparatus 20 (e.g. curing oven). The surface and coating may be manipulated by curing oven for curing and pre-testing manipulation (step 64).

After an appropriate amount of time, IR sensor 30 may take an appropriate field of view picture to measure the radiation emitted (thermal profile) from the shell and the coating (shown at step 66). As referenced herein, "picture" refers to the capture of a single image at a time (t). In another embodiment, IR sensor may take multiple "pictures" or simply scan the field of view over an interval of time.

In taking a picture of the thermal profile, the IR sensor 30 may map an area under a field of view into a grid (i.e. FIG. 2), wherein each square or pixel of the grid may reflect a desired area to measure. For example, the grid may be divided up into land areas of 0.1 mm. Such land area may be based, for example, on the size of a defect normally visible to a casual naked eye, or the smallest size defect which may be practically repairable.

The IR sensor may transmit the measured thermal profile (picture) to a processor (e.g. 40), wherein the processor may compare (step 68) the image with the thermal signature of the automobile shell. In this stage (68) of the method (e.g. Paint Station I, the image captured by IR sensor is compared with the thermal signature created from the raw shell (12 in FIG. 1). More particularly, the grid of the thermal profile viewed and captured by the IR sensor may be electronically overlaid onto the grid of the thermal signature. Deviations between the thermal profile and the thermal signature may be indicated electronically within the processor or visually on a monitor (not shown) by spots of varying color thereby indicating the presence of a defect.

Upon subsequent coatings, as discussed below, the thermal profile of shell and coatings may be compared to a previous thermal profile measured from a shell and fewer coatings, similarly at stage 68. In another embodiment, not only may the captured image be compared with the thermal signature, but it can also be compared to an acceptable preexisting model profile stored within the processor. More particularly, through manual inspection or accumulated data from previous inspections, a model profile (or "standard") indicating a surface coating (and/or ranges of deviations) of acceptable quality may be created and stored within the processor. Accordingly, the thermal profile captured by the IR sensor may be additionally compared to this acceptable model profile for detection of deviations and insuring quality control set to a predetermined standard.

If a defect is indicated upon comparison, the processor may determine (at step 70), based on programmed acceptable standards, whether the defect is of such a nature that it may create a problem for subsequent coatings and/or will result in an unsatisfactory final product (major defect). Where there is a major defect, the processor may then determine at step 72, again based on programmed acceptable standards, whether the defect is repairable by comparing defect parameters with stored data of historic defect phenomenon. If the defect is not repairable, in one embodiment, the shell may be sent for scrap at step 74. If it is determined that the surface and coating is repairable 76, a technician may either repair the defect on the spot, direct the shell to a repair "queue" for handling, or repair the defect later in the coating method (as it may be possible to repair the defect by simply applying the next coat). If repaired, the shell might be re-inserted to the finish method, such as in line for Paint Station II at step 80.

If the processor determines that no major defects are indicated, the automobile shell may pass to Paint Station II (step 80). Similar to Paint Station I, Paint Station II may apply a coating (step 82), transfer shell to curing oven (step 84) and measure the thermal profile of the shell, first coating and second coating (step 86). The IR sensor may transmit the thermal profile to the processor for comparison at step 88. At this stage the processor may compare the thermal profile measured at Paint Station II to the thermal profile measured at Paint Station I for deviations. Deviations among the thermal profiles may indicate defects in the newly applied coating (e.g. coating applied at Paint Station II). In addition, processor may also compare the thermal profile measured at Paint Station II to the thermal signature of the shell or a preexisting model profile (or standard) for an acceptable shell with two coatings in order to further check for defects.

If a major defect is detected as described above, the processor may determine at step 92 whether to send the shell to scrap (step 94) or repair (step 96). If no major defects are indicated, the automobile shell may move to Paint Station III 100 to follow steps similar to steps 80-86 discussed above. The thermal profile measured at Paint Station II, however, can be compared to the thermal profile measured at Paint Stations I and/or II for deviations. In addition, the thermal profile measured at Paint Station III may be compared to the thermal signature of the shell or a preexisting model profile (or standard) for an acceptable shell with three coatings.

Accordingly, in this exemplary method of the present invention, because thermal profiles of each individual coating can be measured and compared not only to previous thermal profiles, but also to the thermal signature of the automobile shell and an acceptable preexisting model profile, defects can be more accurately detected and localized by layer. This detection method may be particularly useful in applications where, despite detection of major defects, the coating method is allowed to continue to or toward completion. In this situation, data regarding each coating layer and detected defects may be compiled so that the defects may be localized and more appropriately repaired as needed at the end of the coating method, rather that at each coating stage. For example, a defect in the top coat might only require a light repair procedure on the topcoat and clear coat, while another defect in the primer layer may need more robust activities.

In some applications, it may be desired to take a single measurement sometime later in the method, or at the completion of the coating method, rather than measuring the thermal profile of each coating. However, defect detection of this type would require a method whereby not only surface defects could be indicated as described above, but also subsurface defects. As such, another aspect of the present invention includes a method for detection and localization of subsurface defects at any point in the coating method, including completion, by taking successive measurements (e.g. pictures of the field of view) of the change in temperature (e.g. thermal contrast) between a defect and its surroundings. In another embodiment, IR sensor may scan the field of view over an interval of time. The measurement in the change of temperature may be compared to an expected change in temperature (e.g. expected thermal contrast) configured from a known thermal emissivity of the particular defect and its surroundings. This method can not only detect a surface defect located in the outermost coating of the paint, but may also detect and localize a defect in any one or more of the coating layers beneath the outermost coating.

Figure 4:
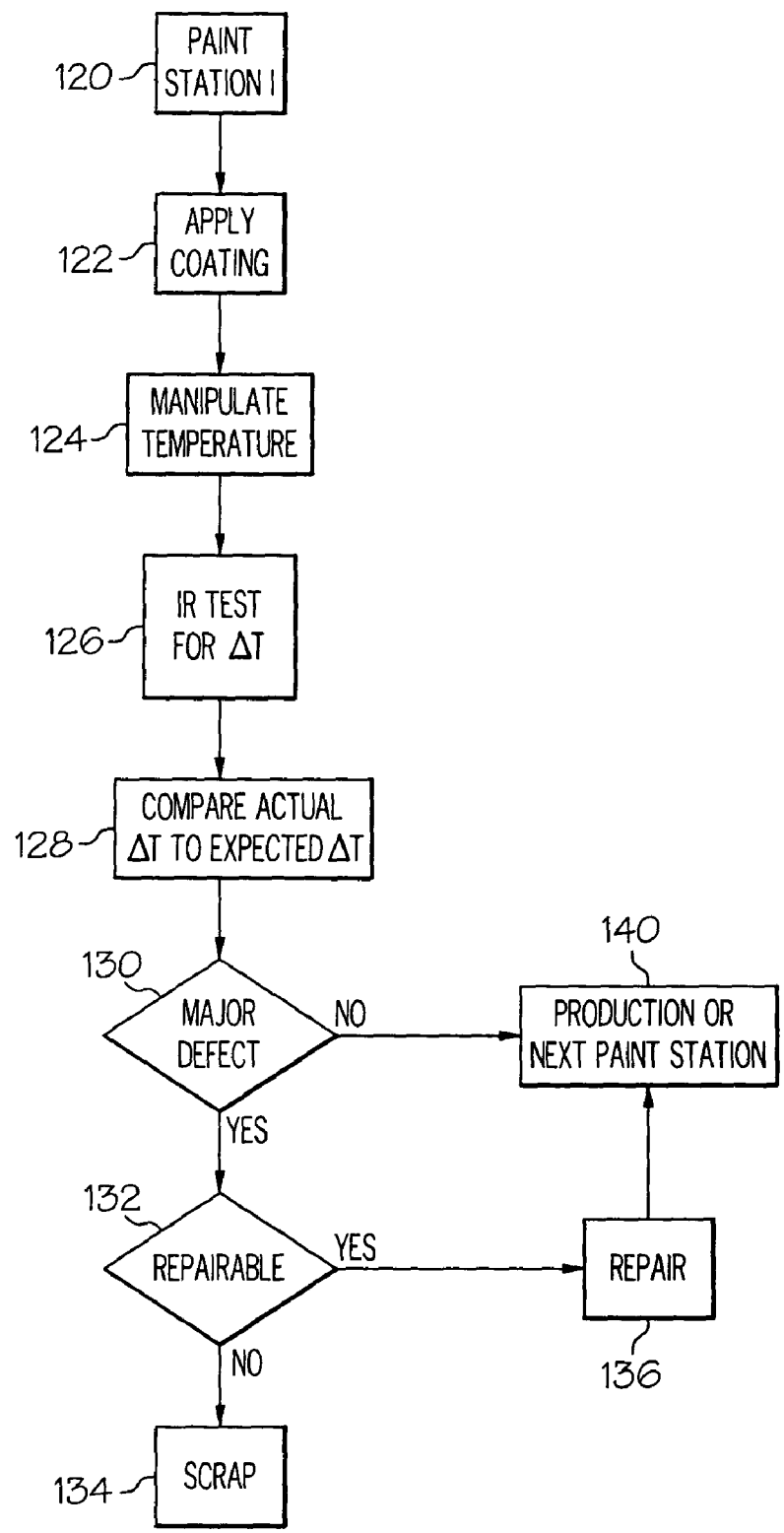
FIG. 4 is a simplified flow chart illustrating exemplary steps in an alternate embodiment of the method of inspecting coatings in accordance with the present invention.

For example, referring to FIG. 4, an alternative method for detecting and localizing surface and subsurface defects is illustrated. As previously discussed, the principle of the inventive method is to measure the changes in temperature of the shell and coatings once heated up in a temperature manipulation apparatus (i.e., curing oven). As illustrated in FIG. 4, a coating may be applied at step 122 to the automobile surface. Once the coating has been applied, the temperature of the automobile shell and coatings may be manipulated 124 as discussed above. Once the coated shell is up to temperature and heating ceases, an IR sensor may measure (at step 126) the speed of the change of temperature of the shell and defects within the coatings at a time when maximum contrast between the defects and their surroundings is achieved. As previously discussed, the thermal effusivity difference between the defect and the surrounding coatings creates a thermal mismatch. The thermal mismatch results in a different thermal wave reflection from the defect as compared with its surroundings, and, as a result, thermal contrast profiles can be established by the IR sensor. Maximum thermal contrast may vary among shells and associated coatings, and timing and specific procedures for measuring the temperatures and changes can be varied accordingly.

The IR sensor may transmit the thermal contrast profiles to the processor, which may be programmed with known thermal effusivity values for the coatings and defects. For example, because a coating and defect may have a known thermal conductivity, density and a specific heat capacitance, an expected change of temperature (how quickly the shell, coatings and defects should change temperature) can be determined. Accordingly, the actual change in temperature from the cooling shell, coatings and defects and the thermal contrast therebetween may be compared to an expected change in temperature to determine the presence of any defects. Similarly, actual change in temperature of detected defects may be compared to programmed data and data accumulated through previous tests to determine the specific type and severity of the defect (i.e., dust, hair, metal flakes, etc.) at stage 130. If no major defect is indicated, then the automobile shell may move to Production or to the next Paint Station (step 140).

Where there is a major defect, the defect may be localized to a specific area at stage 130. As mentioned, IR sensor may map an area under a field of view into a grid, wherein each square or pixel of the grid may reflect a desired area to measure. Processor can compare the speed of the change of temperature of relative adjacent pixels to one another to determine, based on expected change of temperature (discussed above), the location of anomalies (defects). Accordingly, a defect may be localized by both specific coating layer and area.

The processor may then determine at step 132 whether the defect is repairable by comparing defect parameters with stored data of historic defect phenomenon. If the defect is not repairable, in one embodiment, the shell may be sent for scrap at step 134. If it is determined that the surface and coating is repairable, a technician may repair the defect at stage 136 or take other appropriate measures as discussed above.

It should be understood that the method illustrated in FIG. 4 may also be used for detecting defects in a single coating or shell, and therefore, is not limited to application with more than one coating. For example, referring to FIG. 3, wherein a single coating has been applied to the automobile shell, IR sensor may be configured to measure the actual changes in temperature during the measurement period and transmit the measurement to the processor for comparison with a thermal emissivity value (an expected change in temperature) for the shell, coating and defects. Accordingly, the method illustrated in FIG. 4 can be used to detect defects in both single-layered and multi-layered coatings by measurement and comparison of the detected speed of the change in temperature.

Figure 5:
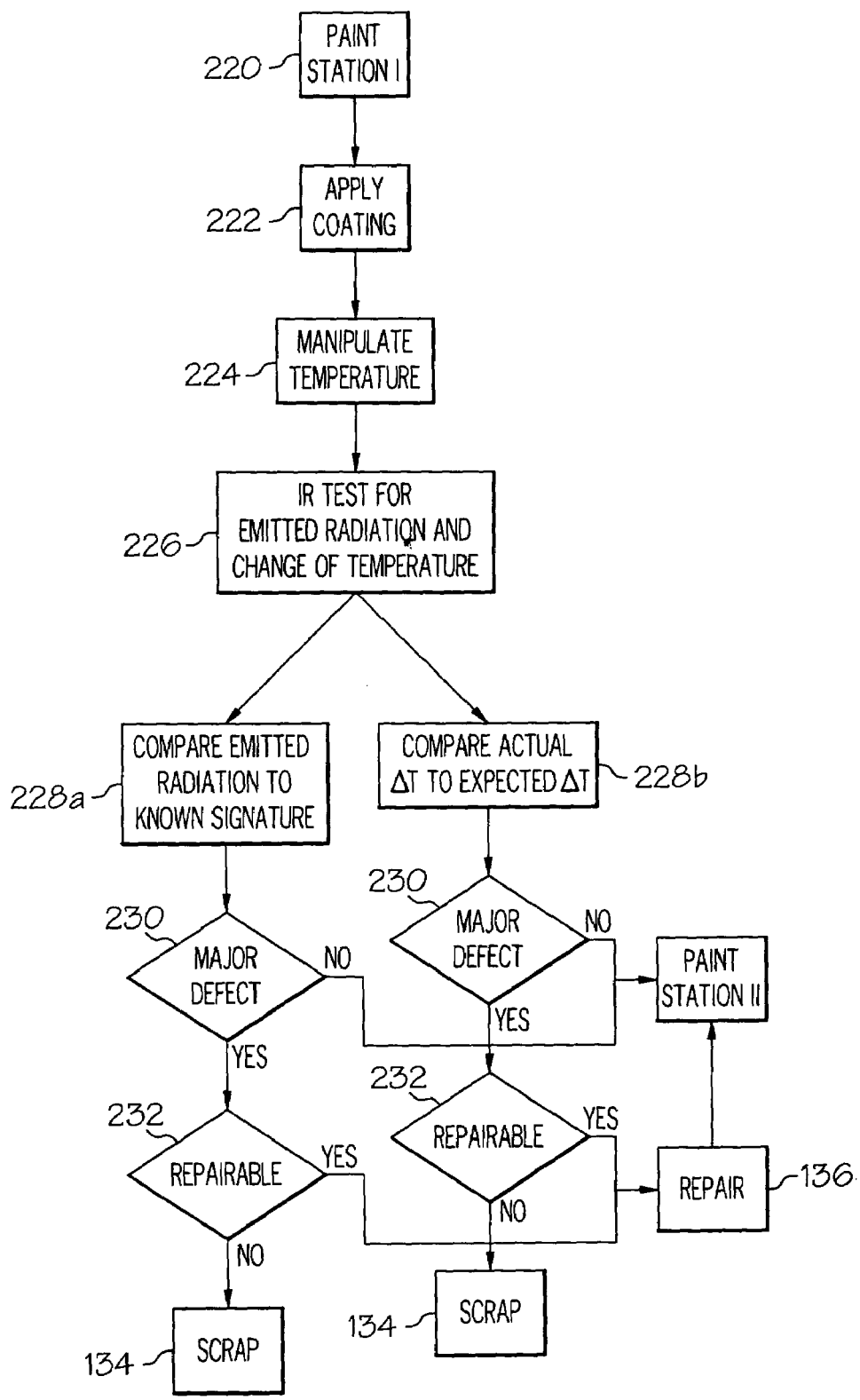
FIG. 5 is a simplified flow chart illustrating exemplary steps in another embodiment of the method of inspecting coatings in accordance with the present invention.

It is also contemplated by the present invention to combine the methods discussed above to further ensure absolute quality of the automobile coating method. For example, referring to FIG. 5, another embodiment of the method for inspecting multi-layered coatings is illustrated. Similar to FIGS. 3 and 4, a coating may be applied (at step 222) to the automobile shell at Paint Station I. Once the coating has been applied, the temperature of the automobile shell and coatings may be manipulated (step 224) as discussed above. Once removed from the curing oven, an IR sensor may take a field of view picture to measure the emitted radiation (thermal profile) from the shell and the coating and may also measure the speed of the change of temperature of the shell and defects within the coatings 226. IR sensor may transmit the data to processor for comparison to stored data.

The processor may compare the thermal profile with the thermal signature of the automobile shell (at step 228*a*), an acceptable preexisting model profile, and/or, if later in the coating method, to the previous thermal profile to determine the presence of any defects. Likewise, the processor may compare the actual change in temperature to an expected change in temperature to determine the presence of any defects (step 228*b*). If desired, the comparisons can be evaluated at step 230 either together or separately to realize the true nature of the defect and whether repair is needed and/or practical.

Because the present systems and method are capable of such detailed measurements and comparisons thereby yielding immediate detection of a defect, it is contemplated that the present invention may be integrated with other artificial intelligence and/or automatic feedback logic so that, once a defect is detected, statistical analysis of operation and necessary changes in coating methods (if any) can be made in real time. For example, referring to FIGS. 2 and 5, upon detection of a defect (i.e. paint over-spray), processor 40 may flag the defect on the current shell for repair, but also transmit a signal to application apparatus 50 at Paint Station I to decrease spray pressure, paint amount, clean or replace the spray gun, etc. (i.e. correct a detected defect). This information might also facilitate maintenance or upgrading of coating application systems by identifying problem areas. In addition, the processor may store and/or otherwise update the knowledge database regarding information about the defect, the operation of the machinery causing the defect and/or the technical operation of the machinery or station where the defect occurred. Accordingly, real time changes and statistical analysis can be made to minimize or eliminate defects, not only in coatings in previous stages, but in the entire coating method.

The foregoing description of the various embodiments of the invention has been presented for the purposes of illustration and description. It is not intended to be exhaustive or to limit the invention to the precise form disclosed. Many alternatives, modifications and variations will be apparent to those skilled in the art of the above teaching. For example, the systems and methods of the present invention may be applied to a variety of coatings in a multitude of applications outside of the automobile coating method. Accordingly, while some of the alternative embodiments of various elements, systems and methods for inspecting single and multi-layered coatings have been discussed specifically, other embodiments will be apparent or relatively easily developed by those of ordinary skill in the art. Accordingly, this invention is intended to embrace all alternatives, modifications and variations that have been discussed herein, and others that fall within the spirit and broad scope of the claims.

What we claim is:

1. A method for detecting defects in coatings comprising the operations of:
   a) applying a plurality of paint process coatings to a surface, wherein the paint process coatings relate to a painting process;
   b) assigning a thermal effusivity value to each of said paint process coatings;
   c) configuring an expected change of temperature for said paint process coatings based on said effusivity values for each of said coatings;
   d) manipulating the temperature of said surface and paint process coatings;
   e) measuring the change of temperature in said manipulated surface and paint process coatings; and
   f) comparing said measured change of temperature in said manipulated surface and paint process coatings to said expected change of temperature so as to detect a defect in said paint process coatings on said surface based upon said effusivity values.

2. The method for detecting defects in coatings as in claim 1, further comprising the operations of:
   a) measuring a thermal profile of said surface to create a thermal signature;
   b) taking a first measurement of radiation emitted from said surface and a first of said coatings;
   c) comparing said emitted radiation to said thermal signature;
   d) taking a second measurement of emitted radiation from said surface and a second of said coatings; and
   e) comparing said first measurement to said second measurement.

3. The method for detecting defects in coatings as in claim 1, further comprising the operation of localizing said defects upon comparison of said measured change of temperature in said manipulated surface and coatings to said expected change of temperature.

4. The method for detecting defects in coatings as in claim 1, further comprising the operation of correcting a defect indicated upon comparison of said measured change of temperature in said manipulated surface and coatings to said expected change of temperature.

5. The method for detecting defects in coatings as in claim 1, further comprising the operation of implementing a change in the operation of an application apparatus to address one or more defects detected.

\* \* \* \* \*